United States Patent [19]

Massie

[11] B 3,992,418

[45] Nov. 16, 1976

[54] PRODUCTION OF PYROMELLITIC DIANHYDRIDE

[75] Inventor: Stephen N. Massie, Palatine, Ill.

[73] Assignee: Universal Oil Products Company, Des Plaines, Ill.

[22] Filed: July 1, 1974

[21] Appl. No.: 485,051

[44] Published under the second Trial Voluntary Protest Program on February 17, 1976 as document No. B 485,051.

[52] U.S. Cl............................ 260/346.4; 260/346.3
[51] Int. Cl.$^2$........................................ C07D 307/89
[58] Field of Search.............. 260/346.4, 346.3, 522, 260/524 R

[56] References Cited
UNITED STATES PATENTS 3,723,516    3/1973    Muller et al. ................. 260/346.4 X

FOREIGN PATENTS OR APPLICATIONS 1,068,649    5/1967    United Kingdom

Primary Examiner—Henry R. Jiles
Assistant Examiner—Bernard I. Dentz
Attorney, Agent, or Firm—James R. Hoatson, Jr.; Raymond H. Nelson; William H. Page, II

[57] ABSTRACT

Pyromellitic dianhydride is produced by reacting pseudocumene with propylene in the presence of an alkylation catalyst, said propylene being present in a stoichiometric excess, to produce 2,4,5-trimethylcumene and diisopropyl-substituted pseudocumenes, treating the resultant 2,4,5-trimethylcumene and diisopropyl-substituted pseudocumenes with an oxygen-containing gas in the presence of a catalyst comprising a vanadium-containing compound dispersed on an inorganic oxide support to produce a treatment product comprising pyromellitic dianhydride and a polycarboxylated compound, decarboxylating the polycarboxylated compound and recovering the resultant pyromellitic dianhydride.

10 Claims, No Drawings

PRODUCTION OF PYROMELLITIC DIANHYDRIDE

The process of this invention relates to the preparation of pyromellitic dianhydride. More specifically, this invention relates to a process for the preparation of pyromellitic dianhydride which comprises reacting pseudocumene with propylene in a stoichiometric excess to produce a mixture comprising 2,4,5-trimethylcumene and diisopropyl-substituted pseudocumenes in the presence of a catalyst comprising a Lewis acid, a mineral acid or a zero-valent molybdenum-carbon monoxide complex, treating the resultant 2,4,5-trimethylcumene and diisopropyl-substituted pseudocumenes mixture with an oxygen-containing gas in the vapor phase in the presence of a catalyst comprising a vanadium-containing compound dispersed on an inorganic oxide support, decarboxylating the polycarboxylated segment of the treatment product and recovering the resultant pyromellitic dianhydride.

It has been shown in the prior art that tetraalkylbenzenes such as 1-isopropyl-2,4,5-trimethylbenzene (also known as 2,4,5-trimethylcumene) have been prepared from the alkylation of pseudocumene with propylene in the presence of an aluminum chloride catalyst. It has also been shown in the prior art that 1-isopropyl-2,4,5-trimethylbenzene may be produced by reacting pseudocumene with propylene in the presence of a compound comprising $AlCl_3$—$CH_3NO_2$—$(CH_3)_2CHX$ wherein X is equal to either chlorine or bromine, said set forth compound to be used as a catalyst. It is also known in the prior art that under the proper oxidation conditions 2,4,5-trimethylcumene may be used as the starting material in the preparation of pyromellitic dianhydrides.

In contradistinction to the prior art it has now been found that pyromellitic dianhydride may be prepared by a process which comprises reacting pseudocumene with a stoichiometric excess of propylene to produce a mixture comprising 2,4,5-trimethylcumene and diisopropyl-substituted pseudocumenes, treating the resultant 2,4,5-trimethylcumene and diisopropyl-substituted pseudocumenes mixture wih an oxygen-containing gas in the presence of a catalyst comprising a vanadium-containing compound dispersed on an inorganic oxide support, decarboxylating the polycarboxylated segment of the treatment product and recovering the resultant pyromellitic dianhydride. The utilization of the above set forth invention will enable the producer of pyromellitic dianhydride to reduce his cost as a result of not having to utilize durene (a very expensive chemical) as the starting material in the preparation of the pyromellitic dianhydride, but allowing the use of pseudocumene and propylene which are relatively inexpensive compounds as the starting materials. Another advantage in the process of the present invention comprises the utilization of the entire reaction mixture of the 2,4,5-trimethylcumene and diisopropyl-substituted pseudocumenes in the preparation of the pyromellitic dianhydrides, in contradistinction to other processes known to the art which require the separation of the 2,4,5-trimethylcumene from the other monopropylation product and 2,3,5-trimethylcumene before oxidation to the resultant pyromellitic dianhydride. The present invention will also allow a recovery of a greater percentage of pyromellitic dianhydride as a consequence of utilization of the entire mixture of the 2,4,5-trimethylcumene and diisopropyl-substituted pseudocumenes as a result of the additional pyromellitic dianhydride which may be prepared from the diisopropyl-substituted pseudocumenes. The oxidation of the diisopropyl-substituted pseudocumenes will produce a benzenepentacarboxylic dianhydride which, upon subsequent strong heating, will be converted by decarboxylation to pyromellitic dianhydride, thereby creating the additional product.

The desired product of the process of this invention, namely, pyromellitic dianhydride is utilized in the chemical industry in many ways. For example, pyromellitic dianhydride is the valuable intermediate in the formation of high temperature-resistant polymers, laminates, molds and coatings; as a cross-linking agent for epoxy plasticizers in vinyls; in the preparation of alkyl resins; in the preparation of nonfogging plasticizers; in high temperature lubricants and intermediates.

It is therefore an object of this invention to provide a process for the preparation of pyromellitic dianhydride.

A further object of this invention is to provide a process for the preparation of pyromellitic dianhydrides utilizing certain procedures which will permit a greater recovery of the desired compound in a more expedient manner.

In one aspect an embodiment of this invention resides in a process for the preparation of pyromellitic dianhydride which comprises reacting pseudocumene with propylene, said propylene being present in a stoichiometric excess at reaction conditions in the presence of a catalyst comprising a Lewis acid, a mineral acid or a zero-valent molybdenum-carbon monoxide complex to produce 2,4,5-trimethylcumene and diisopropyl-substituted pseudocumenes, treating the resultant 2,4,5-trimethylcumene and diisopropyl-substituted pseudocumenes with an oxygen-containing gas in the presence of a catalyst comprising a vanadium-containing compound dispersed on an inorganic oxide support at treatment conditions, decarboxylating the polycarboxylated treatment product at decarboxylation conditions to produce pyromellitic dianhydride and recovering the resultant pyromellitic dianhydride.

A specific embodiment of this invention resides in a process for preparing pyromellitic dianhydride which comprises reacting pseudocumene with propylene in the presence of anhydrous hydrogen fluoride, said propylene being present in a mol ratio of 1.5 mols of propylene per 1 mol of pseudocumene, at a temperature of 50°C and at autogenous pressure to produce a mixture comprising 2,4,5-trimethylcumene, 3,6-diisopropylpseudocumene and 3,5-diisopropylpseudocumene, treating the resultant 2,4,5-trimethylcumene, 3,6-diisopropylpseudocumene and 3,5-diisopropylpseudocumene with air in the presence of a vanadium pentoxide catalyst which has been dispersed on an alumina support at conditions which include a temperature of about 350°C and a pressure of 1 atmosphere, decarboxylating any polycarboxylic compound in the treatment product at a temperature of about 550°C and at autogenous pressure to produce pyromellitic dianhydride and recovering the resultant pyromellitic dianhydride.

Other objects and embodiments will be found in the following further detailed description of the present invention.

As hereinbefore set forth the present invention is concerned with a process for preparing pyromellitic dianhydride, said process being effected by reacting pseudocumene with a stoichiometric excess of propylene to produce a mixture comprising 2,4,5-trimethylcumene and diisopropyl-substituted pseudocumenes, treating the resultant mixture comprising 2,4,5-trimethylcumene and diisopropyl-substituted pseudocumenes with an oxygen-containing gas in the presence of a catalyst comprising a vanadium-containing compound dispersed on an inorganic oxide support at treatment conditions, decarboxylating any polycarboxylic compound segment of the treatment product to produce pyromellitic dianhydride and recovering the resultant pyromellitic dianhydride. The reaction of the pseudocumene with the stoichiometric excess of propylene is effected under reaction conditions which include temperatures in the range of from about 0° to about 150°C and a pressure of from about 1 atmosphere to about 100 atmospheres. When superatmospheric pressures are employed, said pressure may be afforded by the introduction of a substantially inert gas such as nitrogen or helium into the autoclave or reaction zone. The treatment of the resultant mixture comprising 2,4,5-trimethylcumene and the diisopropyl-substituted pseudocumenes with an oxygen-containing gas in the presence of a catalyst comprising a vanadium-containing compound dispersed on an inorganic oxide support is effected at treatment conditions, said treatment conditions including a temperature of from about 100° to about 500°C and a pressure of from about 1 atmosphere to about 100 atmospheres. The polycarboxylated segment of the treatment product is subjected to decarboxylation to produce pyromellitic dianhydride at decarboxylation conditions which include a temperature of from about 450° to about 600°C at atmospheric pressure or a temperature of from about 270° to about 400°C at subambient pressures. Another variable which is employed in the reaction of the propylene with the pseudocumene is the amount of reactants, the propylene being present in a stoichiometric molar excess in the range of from about 1.1 mols of propylene to about 2.0 mols of propylene per mole of pseudocumene and preferably 1.5 mols of propylene to about 2.0 mols of propylene per mol of pseudocumene. It is also contemplated within the scope of this invention that propylene may be present in a molar ratio in excess of 2.0 mols of propylene per mol of pseudocumene, however, such reactant variables are usually considered not to be economically feasible. The preferred ratio of propylene to pseudocumene is the quantity of propylene necessary to insure a complete conversion of the 2,3,5-trimethylcumene to a diisopropylpseudocumene in the propylene-pseudocumene reaction.

The reaction of the propylene with the pseudocumene is effected in the presence of a catalyst comprising a Lewis acid, a mineral acid or a zero-valent molybdenum-carbon monoxide complex, said group of catalyst commonly referred to as alkylation catalysts. Suitable examples of Lewis acids will include boron trifluoride, aluminum chloride, aluminum bromide, ferric chloride, molybdenum pentachloride, etc. Suitable examples of mineral acids would include hydrogen fluoride, sulfuric acid, phosphoric acid, solid phosphoric acid, etc. while it is also contemplated that a Lewis acid may be utilized in conjunction with a mineral acid to improve catalytic activity, such as the use of boron trifluoride with hydrogen fluoride. Another suitable alkylation catalyst comprises a zero-valent molybdenum-carbon monoxide complex such as benzene molybdenum tricarbonyl, toluene molybdenum tricarbonyl, o-xylene molybdenum tricarbonyl, m-xylene molybdenum tricarbonyl, p-xylene molybdenum tricarbonyl, cumene molybdenum tricarbonyl, mesitylene molybdenum tricarbonyl, molybdenum tricarbonyl, etc.

The decarboxylation of any initially-formed polycarboxylic compound comprising benzenepentacarboxylic dianhydride to pyromellitic dianhydride may be performed within the treatment step where the temperatures are maintained at a higher level than necessary for oxidation.

The reactants of the above set forth invention comprise propylene as set forth in Structure I below

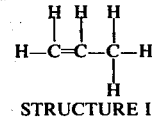

STRUCTURE I and pseudocumene as set forth in Structure II

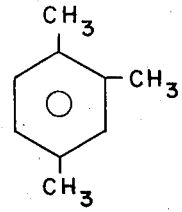

STRUCTURE II

The reaction of the pseudocumene with the stoichiometric excess of propylene produces a mixture comprising 2,4,5-trimethylcumene and three isomers of diisopropyl-substituted pseudocumenes as represented in Structures III, IV, and V below

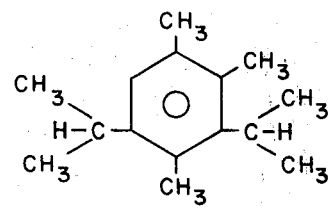

STRUCTURE III

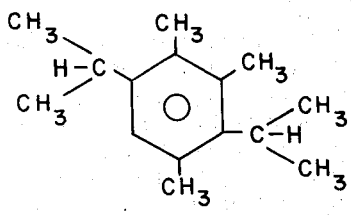

STRUCTURE IV

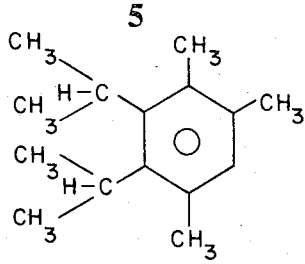

STRUCTURE V wherein Structure III is named as 3,5-diisopropylpseudocumene, Structure IV is named as 3,6-diisopropylpseudocumene and Structure V is named as 5,6-diisopropylpseudocumene. However, it should be noted that the formation of the 5,6-isomer is remote as a result of steric hindrance.

The oxygen-containing gas utilized in the treatment of the resultant mixture comprising 2,4,5-trimethylcumene and the diisopropyl-substituted pseudocumenes will comprise any gas which contains oxygen such as oxygen, air, oxygen and nitrogen mixtures, oxygen and helium mixtures, oxygen and argon mixtures, etc. Suitable examples of catalysts comprising vanadium-containing compounds would include vanadium pentoxide, vanadium chloride, vanadium bromide, vanadium iodide, etc. It is contemplated within the scope of this invention that the vanadium-containing compound is dispersed on an inorganic oxide support. Examples of inorganic oxide supports would include alumina, silica, magnesia, zirconia, thallia, a mixture of silica-alumina, pumice, etc. It is understood that the aforementioned Lewis acids, mineral acids, molybdenum-carbon monoxide complexes, vanadium-containing compounds, oxygen-containing gases and inorganic oxide supports are only representative of the class of compounds which may be employed and that the present invention is not necessarily limited thereto.

It is contemplated within the scope of this invention that the process for the preparation of the pyromellitic dianhydrides may be performed in a continuous manner of operation. When such a type of operation is employed the reactants comprising pseudocumene and the excess stoichiometric amount of propylene are charged to a reaction vessel maintained at predetermined conditions of temperature and pressure. After completion of the desired residence time, the pseudocumene and propylene react to form a mixture comprising 2,4,5-trimethylcumene and diisopropyl-substituted pseudocumenes. The resultant 2,4,5-trimethylcumene and diisopropyl-substituted pseudocumenes are continuously withdrawn and subsequently charged to a second treatment zone wherein they are treated with an oxygen-containing gas in the presence of a catalyst comprising a vanadium-containing compound dispersed on an inorganic oxide support at elevated temperatures and predetermined pressures so as to form pyromellitic dianhydride which may be recovered as the effluent stream. It is also contemplated within the scope of this invention that the polycarboxylated compound comprising any benzenepentacarboxylic dianhydride which is formed from the treatment of the oxygen-containing gas in the presence of a catalyst comprising a vanadium-containing compound dispersed on the inorganic oxide support with the diisopropyl-substituted pseudocumene species of the resultant mixture is decarboxylated at decarboxylation conditions to produce pyromellitic dianhydride. It is, however, contemplated that the decarboxylation and total pyromellitic dianhydride production may occur in the treatment of the mixture comprising 2,4,5-trimethylcumene and diisopropyl-substituted pseudocumenes. The process of this invention may also be performed in a batch-type operation although the continuous mode of operation is preferred.

Inasmuch as the treatment catalytic composition of matter may be solid in nature the process may be effected utilizing a catalytic fixed bed of operation in which the 2,4,5-trimethylcumene and the diisopropyl-substituted pseudocumenes may be passed over said fixed bed at treatment conditions to produce the desired pyromellitic dianhydride.

The pyromellitic dianhydride which may be prepared according to the process of this invention may be exemplified by Structure VI.

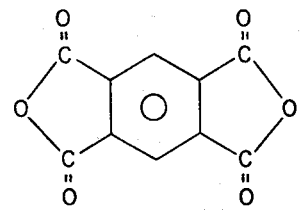

STRUCTURE VI

The following examples are given to illustrate the process of the present invention which, however, are not intended to limit the generally broad scope of the present invention in strict accordance therewith.

EXAMPLE I

In this example 1.0 mols of pseudocumene, 1.5 mols of propylene and 300 grams of hydrogen fluoride are placed in a sealed 1000 ml stirred autoclave provided with heating means. The autoclave is heated to a temperature of 50°C and maintained thereat at autogenetic pressure for a period of time comprising 5 hours. Upon completion of the 5 hour period of time, the heating is discontinued and the autoclave allowed to return to room temperature. The organic layer of the flask is divided into two segments, one of which is subjected to analysis by gas-liquid chromatography instrumentation, said analysis disclosing the product to be a mixture of 2,4,5-trimethylcumene, 3,5-diisopropylpseudocumene and 3,6-diisopropylpseudocumene. The second segment of the reaction product is charged to a separate autoclave which is pressed with 45 atmospheres of air and is heated to a temperature of 350°C, said autoclave containing vanadium pentoxide dispersed on an alumina support. The autoclave is maintained under these conditions for a period of time comprising 3 hours, at the end of which time the heating is discontinued and the autoclave is allowed to return to room temperature. The product is recovered from the autoclave and subjected to analysis of the methyl ester-derivatives by gas-liquid chromatographic instrumentation, said analysis disclosing the presence of pyromellitic dianhydride and benzenepentacarboxylic dianhydride. The reaction mixture is subsequently recharged to a decarboxylation vessel fitted with a sublimation condenser and the vessel is heated to 300°C at 1 mm mercury for an additional 1 hour period of time. At the end of the 1 hour period of time, the heating is discontinued and the vessel is allowed to return to room temperature. The decarboxylation product is again recovered from the decarboxylation vessel and subjected to analysis of the type hereinbefore set forth with gas-liquid chromatographic instrumentation, said analysis disclosing a greater percentage of pyromellitic dianhydride and a smaller quantity of benzenepentacarboxylic dianhydride than originally found in the first analysis.

EXAMPLE II

In this example a continuous process is maintained for the production of the pyromellitic dianhydride as hereinafter set forth. A reaction zone containing aluminum chloride is maintained at a temperature of 100°C and a pressure of 50 atmospheres as afforded by the introduction of a substantially inert gas, namely, nitrogen. One (1) mol of pseudocumene and 1.75 mols of propylene are charged to the reaction zone, said zone being provided with heating means. The reaction zone is maintained at a temperature of 100°C so as to afford a residence time for the pseudocumene and propylene of approximately 25 minutes. At the end of the 25 minute period of time, the reaction products of the propylene and the pseudocumene, namely, 2,4,5-trimethylcumene and the isomers of diisopropyl-substituted pseudocumenes are withdrawn from the reaction zone and charged to a subsequent treatment zone, said treatment zone being maintained at a pressure of 100 atmospheres as afforded by the introduction of air and a temperature of 325°C. The treatment zone contains a catalyst comprising vanadium chloride dispersed on a silica support for a period of time so as to afford the 2,4,5-trimethylcumene and the isomers of diisopropyl-substituted pseudocumene a residence time of approximately 1 hour within the treatment zone. At the end of the 1 hour residence time the reaction product is withdrawn and passed through a quartz bead-packed zone, heated at 500°C for a residence time of 0.5 hours, condensed and the methyl ester-derivatives are analyzed by means of gas-liquid chromatography, said analysis disclosing the product to be pyromellitic dianhydride.

EXAMPLE III

In this example a continuous process for the preparation of pyromellitic dianhydride is maintained as hereinafter set forth. A reaction zone containing benzene molybdenum tricarbonyl is maintained at a temperature of 150°C and a pressure of 50 atmospheres as afforded by the introduction of a substantially inert gas, namely, helium. One (1) mol of pseudocumene and 1.7 mols of propylene are charged to the reaction zone, said zone being maintained for a period of time so as to afford a residence time for the reaction of the pseudocumene and propylene of approximately 30 minutes. At the end of the 30 minute period of time the resultant mixture of products from the pseudocumene and the propylene, namely 2,4,5-trimethylcumene and the isomers of diisopropyl-substituted pseudocumene are withdrawn from the reaction zone and charged to a subsequent treatment zone. The treatment zone is maintained at a temperature of 350°C and a pressure of 50 atmospheres as afforded by the introduction of substantially pure oxygen, said treatment zone containing a catalyst comprising vanadium pentoxide dispersed on an alumina support catalyst. The treatment zone is maintained at the above set forth physical conditions of temperature and pressure for a period of time so as to afford a residence time of approximately 1 hour for the mixture comprising 2,4,5-trimethylcumene and the diisopropyl-substituted pseudocumenes. The reaction product is recovered from the treatment zone and subject to analysis by gas-liquid chromatography, said analysis disclosing the presence of pyromellitic dianhydride. The oxidation product which is recovered from treatment zone is charged to a decarboxylation zone maintained at a temperature of 265°C at a pressure of 2 mm of mercury. The carboxylated product is allowed a residence time of 25 minutes, after which the decarboxylated product is recovered and analyzed by means of gas-liquid chromatographic instrumentation, said analysis disclosing the product to be pyromellitic dianhydride.

I claim as my invention:

1. A process for the preparation of pyromellitic dianhydride which comprises
   a. treating pseudocumene with propylene, said propylene being present in a stoichiometric excess, at a temperature of from about 0° to about 150°C and a pressure of from about 1 atmosphere to about 100 atmospheres in the presence of a catalyst comprising a Lewis acid, a mineral acid or a zero-valent molybdenum-carbon monoxide complex to product 2,4,5-trimethylcumene and diisopropyl-substituted pseudocumenes;
   b. treating the resultant 2,4,5-trimethylcumene and diisopropyl-substituted pseudocumenes with an oxygen-containing gas in the presence of a catalyst comprising a vanadium-containing compound dispersed on an inorganic oxide support at a temperature of from about 100° to about 500°C and a pressure of from about 1 atmosphere to about 100 atmospheres;
   c. decarboxylating the polycarboxylated treatment product at a temperature of from about 450° to about 600°C at atmospheric pressure or a temperature of from about 270°C to about 400°C at subambient pressures to produce pyromellitic dianhydride; and
   d. recovering the resultant pyromellitic dianhydride.

2. The process of claim 1 further characterized in that the oxygen-containing gas is oxygen.

3. The process of claim 1 further characterized in that the oxygen-containing gas is air.

4. The process of claim 1 further characterized in that the vanadium-containing compound is vanadium pentoxide.

5. The process of claim 1 further characterized in that the vanadium-containing compound is vanadium chloride.

6. The process of claim 1 further characterized in that the inorganic oxide support is alumina.

7. The process of claim 1 further characterized in that the inorganic oxide support is silica.

8. The process of claim 1 further characterized in that the Lewis acid is aluminum chloride.

9. The process of claim 1 further characterized in that the mineral acid is hydrogen fluoride.

10. The process of claim 1 further characterized in that zero-valent molybdenum-carbon monoxide complex is benzene molybdenum tricarbonyl.

* * * * *